United States Patent [19]
Stein et al.

[11] 3,963,440
[45] June 15, 1976

[54] ANALYSIS SYSTEM

[75] Inventors: Bernard Stein, Andover; Philip Spergel, Lexington, both of Mass.

[73] Assignee: Instrumentation Laboratory, Inc., Lexington, Mass.

[22] Filed: June 27, 1974

[21] Appl. No.: 483,610

[52] U.S. Cl. .......................... 23/253 R; 23/255 E; 204/195 P; 324/30 R
[51] Int. Cl.² .................. G01N 27/00; G01N 31/00; G01N 33/16
[58] Field of Search ............. 23/253 R, 259, 230 B; 204/195 P; 324/29, 30 R, 30 US

[56] References Cited
UNITED STATES PATENTS

| | | | |
|---|---|---|---|
| 3,556,950 | 1/1971 | Dahms | 23/253 R X |
| 3,658,478 | 4/1972 | Spergel et al. | 23/253 R |
| 3,672,843 | 6/1972 | Rosse et al. | 23/253 R |

*Primary Examiner*—Joseph Scovronek

[57] ABSTRACT

A blood analysis system comprises a tempering chamber in which a plurality of flow through measuring cells are disposed. A sensor electrode is associated with each cell. A sample flow path extends from an entrance port through a heater element, a first measuring cell, a control valve, a second measuring cell, a reference electrode interface, to a positive displacement pump. In standby condition, the entrance port is immersed in flush fluid and operation of the pump in such condition flows flush fluid through the entire sample path. Fluid access to either measuring cell is obtainable through the entrance port, auxiliary valve ports, or disconnectable conduits connected to the valve. The control valve is connected in the flow path between the two measuring cells, and in a first condition that control valve places the measuring cells in series fluid communication with the inlet port, and in a second condition isolates the measuring cells from one another so that the electrode systems associated with the two measuring cells may be calibrated concurrently and independently of one another.

15 Claims, 19 Drawing Figures

FIG 4

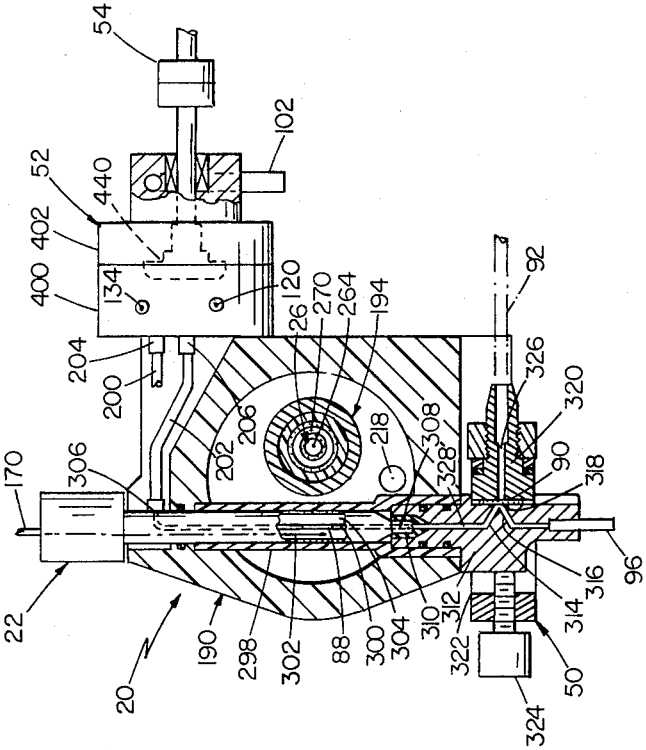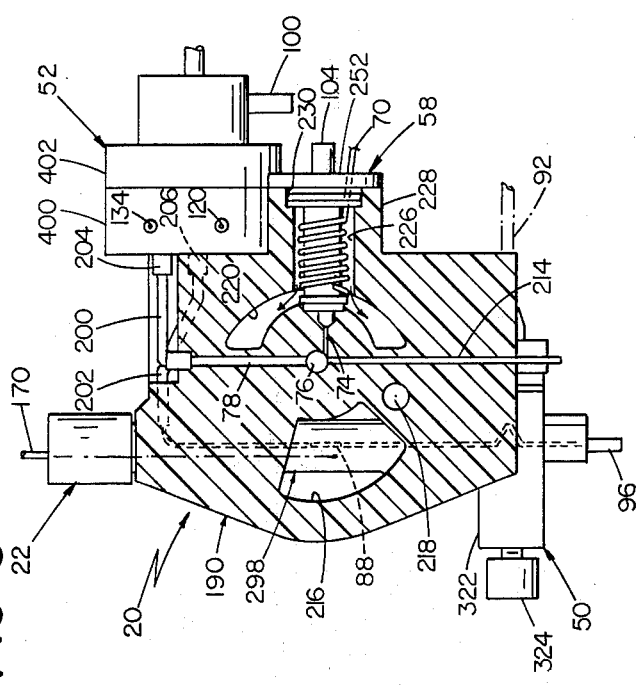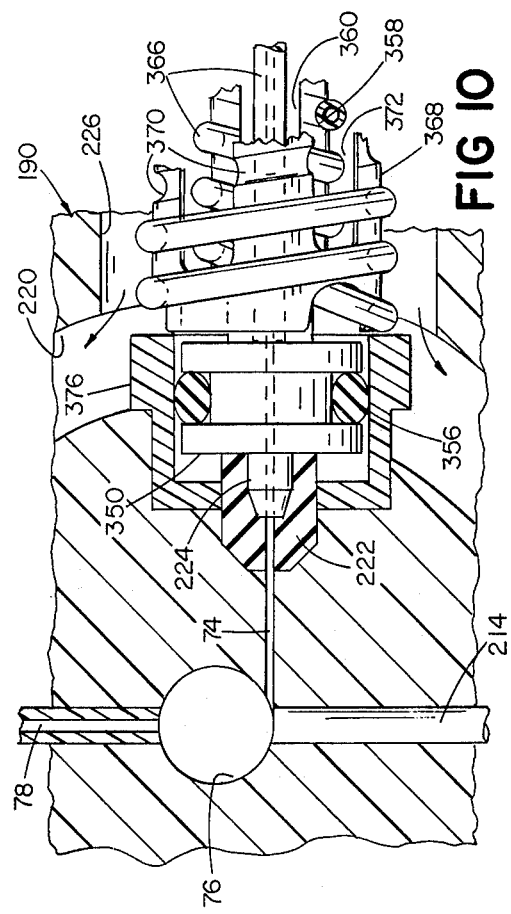

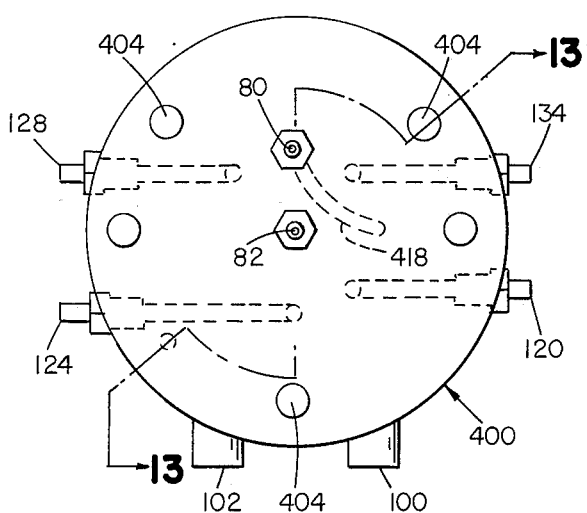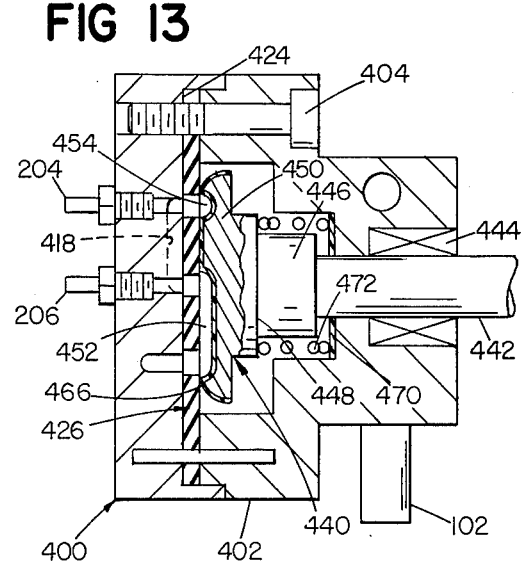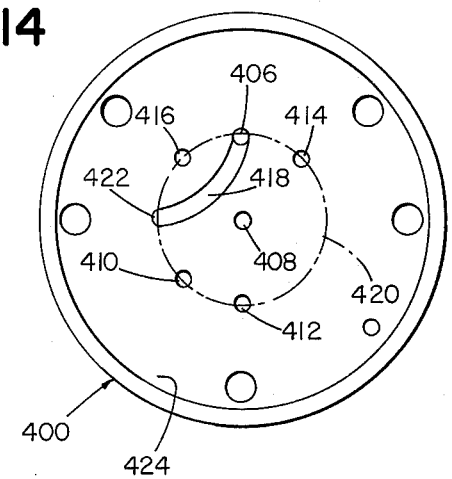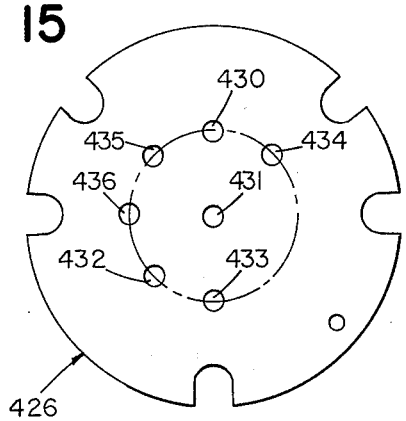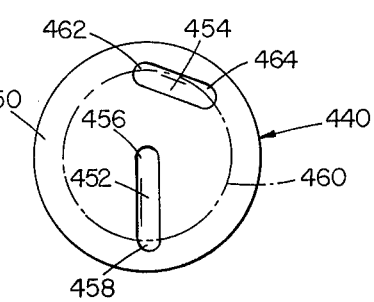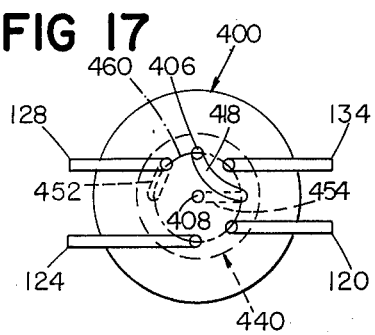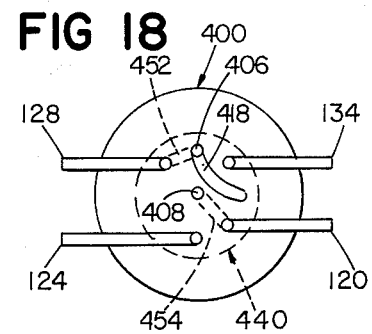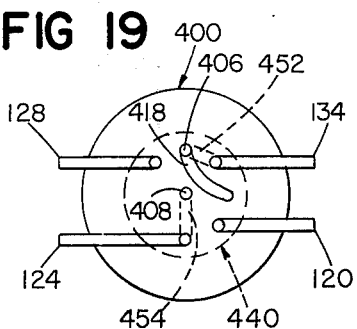

ANALYSIS SYSTEM

SUMMARY OF THE INVENTION

This invention relates to apparatus for analysis of fluid samples and has particular application to apparatus for the analysis of parameters of precious fluids such as blood.

Frequently it is desired to obtain an accurate measurement of two or more constituents of a fluid sample of small volume. For example, the values of particular constituents of a blood sample may be useful in providing diagnostic information or for the control of life support devices. In particular instances, pH, $PCO_2$ and $PO_2$ values of blood specimens provide important clinical information. Various analysis systems employing electrochemical electrodes have been developed for such analyses. For example, a blood analysis system is shown in Spergel et al. U.S. Pat. No. 3,658,478 which employs a first sample input to a pH measuring system and a second sample input to a carbon dioxide and oxygen measuring system. Other blood analysis instruments have employed a single inlet plural measuring cell arrangements. The fluid to be analyzed must frequently be brought to and maintained at a desired stable measuring temperature. Measurement electrode systems in such apparatus are temperature sensitive. For example, blood samples to be analyzed are frequently refrigerated and exposure of electrode assemblies for the measurement of partial pressures of carbon dioxide and oxygen to the refrigerated blood sample degrades the response of such electrode assemblies. It is frequently desirable to measure parameters of a sample of small volume with promptness and accuracy and it is an object of this invention to provide an improved arrangement of measuring chambers and electrode systems which facilitates the measurement of a plurality of parameters of a single precious fluid sample of small volume.

Another object of this invention is to provide novel and improved fluid handling systems for use in fluid analysis apparatus.

Another object of the invention is to provide a novel and improved fluid sample analysis instrument.

Still another object of the invention is to provide a novel and improved fluid handling system for the analysis of parameters of precious fluids such as blood.

In accordance with the invention there is provided a fluid analysis system that includes a tempering chamber in which a plurality of flow through measuring cells are disposed. A constituent sensor is disposed for sensing relation with fluid in each cell. Each measuring cell has an inlet and an outlet and the system has a sample entrance port that is connected to the inlet ports of both cells. The outlet ports of both cells are connected to a positive displacement pump, the operation of which pumps fluid through both cells concurrently. The sample entrance port is movable between a first position exposed to receive a sample to be analyzed and a second position immersed in flush fluid. Operation of the common pump moves fluid (either sample fluid or flush fluid) through both chambers in coordinated manner.

In preferred embodiments, the system includes a flow control device mounted directly on the tempering chamber. The flow control device is connected between the two measuring cells and has four auxiliary inputs to which different calibrating fluids are supplied. In a first mode the flow control device channels fluid sample from one measuring cell to the second measuring cell; in a second mode calibrating fluid is channelled from one auxiliary input for flow through one measuring cell and calibrating fluid is channeled from a second auxiliary input for flow through the second measuring cell; and in a third mode different calibrating fluids from the third and fourth auxiliary inputs are channelled to the measuring cells. Exposed detachable conduit connections extend between the control device and each measuring cell, thus facilitating alternate access to the measuring cells as desired.

In a particular embodiment, sensors for measuring $PCO_2$ and $PO_2$ of a blood sample are coupled to one measuring cell and a pH sensor is connected to the other measuring cell. Associated with the pH sensor is a reference electrode interface, which interface is also mounted directly on the tempering chamber. The sample is introduced through a heater stage which is inserted into the tempering chamber and tempering fluid is flowed through the heater stage prior to entrance into the tempering chamber. The temperature of the tempering fluid is accurately controlled to maintain both measuring cells at an accurate, stable temperature. In the case of blood analyses, this temperature is typically 37°C. The total volume of the operative sample flow path for simultaneous measurements using both cells is preferably less than 500 microliters and the configuration of the sample flow path in the particular embodiment is such that its volume is about 350 microliters, that is the volume between the sample heater and the reference electrode interface (through the first measuring cell, the flow control device, and the second measuring cell). The positive displacement pump and/or the flow control device may be operated automatically or manually. An even smaller sample volume may be placed in one measuring cell and then the second measuring cell for serial analysis by manual operation of the pump.

The invention enables analysis of samples of small fluid volume in a compact modular arrangement which is easy to use and can be operated in several different modes and which can be easily, rapidly and thoroughly flushed and which quickly provides accurate analysis data.

Other objects, features and advantages of the invention will be seen as the following description of a particular embodiment progresses, in conjunction with the drawings, in which:

FIG. 4 is a schematic diagram showing fluid flow paths of the blood analysis instrument shown in FIG. 1;

FIG. 8 is a sectional view taken along the line 8—8 of FIG. 5;

FIG. 9 is a sectional view taken along the line 9—9 of FIG. 5;

FIG. 10 is an enlarged sectional view showing details of the interconnection between the sample heater and a measuring cell;

FIG. 11 is a sectional view of the sample heater;

FIG. 12 is a bottom view of the flow control valve;

FIG. 13 is a sectional view of the flow control valve taken along the line 13—13 of FIG. 12;

FIG. 14 is a top view of the base of the valve;

FIG. 15 is a top view of the sealing disc employed in the valve;

FIG. 16 is a bottom view of the selector disc employed in the valve; and

FIGS. 17, 18 and 19 are diagrammatic bottom views showing the valve in three different positions.

DESCRIPTION OF PARTICULAR EMBODIMENT

Figure 1:
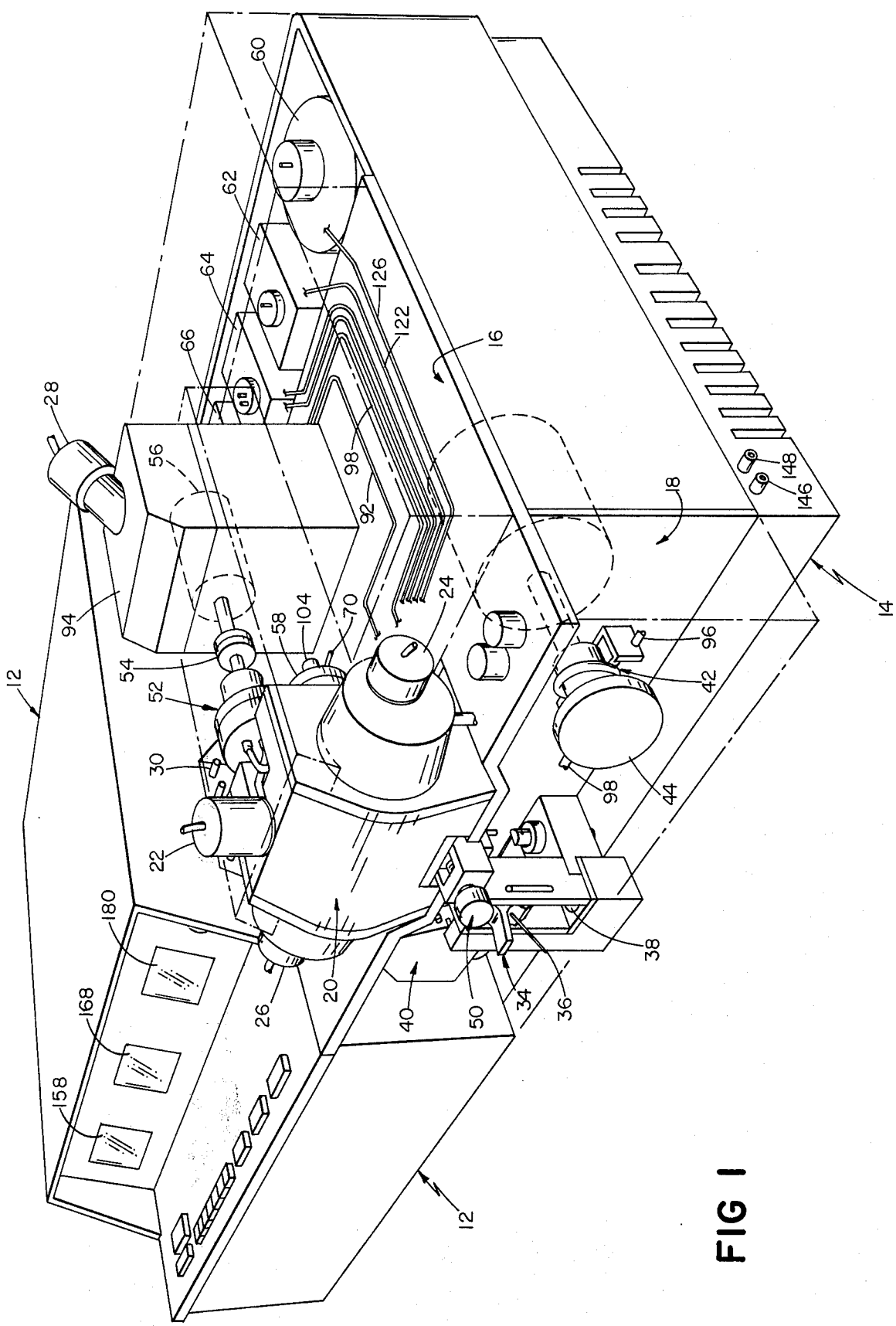
FIG. 1 is a perspective diagrammatic view of a blood analysis system constructed in accordance with the invention.
Figure 3:
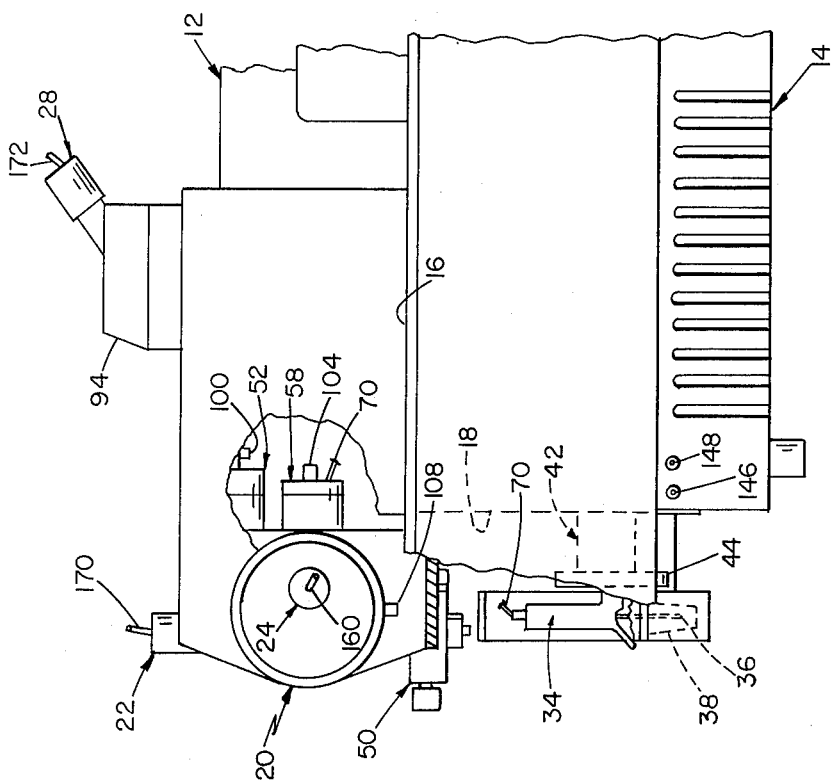
FIG. 3 is an end view, with parts broken away, of the system shown in FIG. 1.
Figure 2:
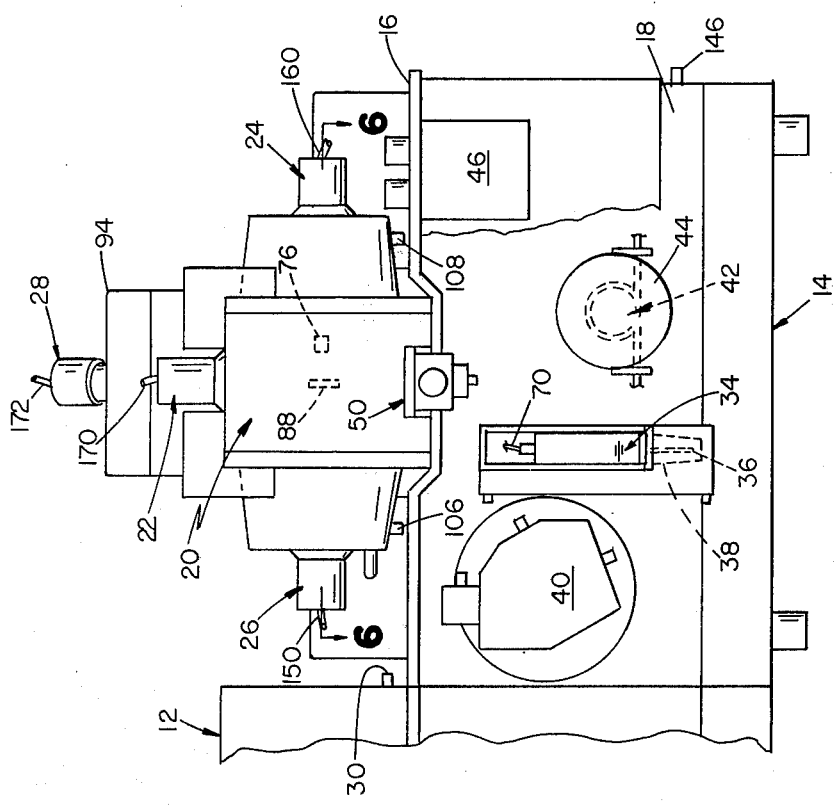
FIG. 2 is a front elevational view with parts broken away of the fluid control portion of the system shown in FIG. 1.

A perspective view of a blood gas analysis instrument in accordance with the invention is shown in FIG. 1 and front and end views of the fluid handling section are shown in FIGS. 2 and 3. The instrument includes an electronics section 12 that includes a set of controls and above the set of controls are three digital displays 158, 168 and 180 for displaying $PCO_2$, $PO_2$ and pH values and a fluid handling section 14 that includes a top plate 16 and a front plate 18. Mounted on plate 16 is a tempering chamber tank assembly 20 which carries a pH electrode 22, an oxygen electrode 24 and a carbon dioxide electrode 26. A reference electrode 28 is mounted to the rear of tank assembly 20. Cables connect the outputs from electrodes 22, 24, 26 and 28 to terminal interface 30 with the electronics section 12.

Mounted on the front plate 18 is a sample mechanism 34 that includes a sample tip 36 mounted for movement between a first position as shown in FIG. 1 exposed for induction of a sample and a second position where tip 36 is immersed in flush fluid in chamber 38. Also mounted on panel 18 is a circulator 40, a motor driven peristaltic pump structure 42 to which is also coupled to a manually operable drive disc 44, and bubble chamber structure 46. Immediately below tank 20 is a removable reference electrode interface or leak junction structure component 50. Mounted on the rear of tank 20 is a control valve 52 and extending rearwardly from valve 52 is valve drive shaft 54 that is driven by stepper motor 56. Disposed at the rear of tank 20 is sample heater structure 58. At the rear of the fluid handling section is a first buffer supply 60, a second buffer supply 62, a supply 64 of flush fluid and a waste container 66.

Figure 4:
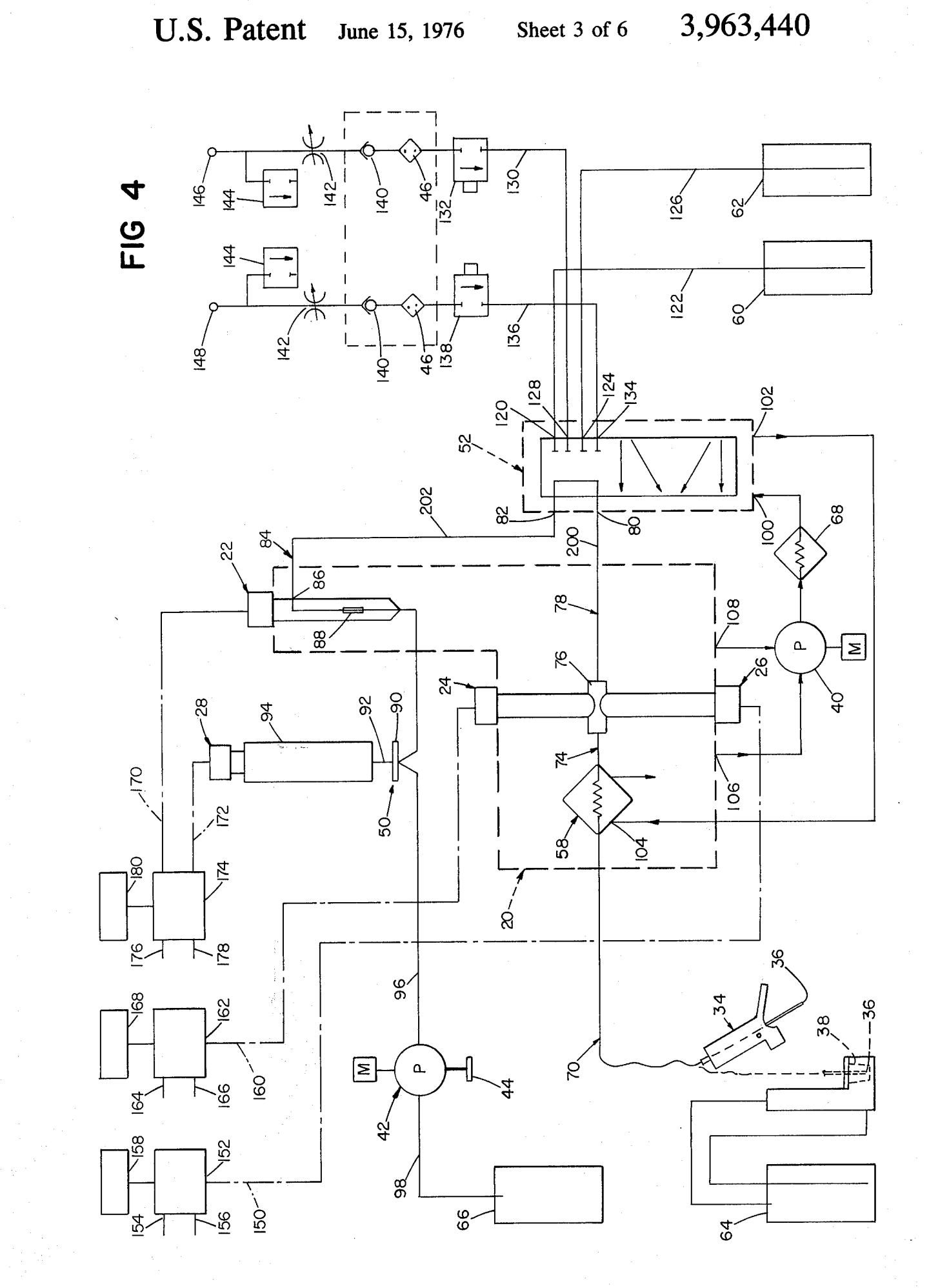

Further details of fluid flow paths may be seen with reference to the schematic diagram in FIG. 4. As there shown, flush chamber 38 is connected to supply 64. The sample entrance (inlet probe tip 36) is connected via conduit 70 to sample heater 58 which extends into tank 20. Flow path 74 extends from sample heater 58 into inlet measuring cell 76 to which end surfaces of electrode system 24 and 26 are exposed. Flow path 78 from cell 76 extends to port 80 of valve 52 and valve port 82 is connected by conduit 84 to port 86 in pH electrode 22. The flow path is through a capillary passage that includes a measuring cell section 88 of pH sensitive glass to leak junction structure 50. That structure carries a membrane 90 to which electrolyte is supplied over conduit 92 from KCl reservoir 94 in which the pH reference electrode 28 is disposed. The sample flow path continues from leak junction structure 50 over conduit 96 to peristaltic pump 42 and from pump 42 over line 98 to waste container 66.

Thermostatically controlled water, typically at a temperature of 37°C, is circulated by circulator 40 through heater 68 and conduit 100 to the housing of valve 52 and from that housing over conduit 102 to the inlet 104 of sample heater. The water is flowed over the sample flow tubing in the heater structure and into the water jacket of tempering chamber 20 that surrounds the electrodes 22, 24 and 26. Water from jacket 20 is returned over lines 106 and 108 to circulator 40.

Calibrating fluids are supplied to chambers 76 and 88 through valve 52. Valve 52 has a first port 120 connected by a conduit 122 to first buffer reservoir 60; a second port 124 connected by conduit 126 to a second buffer reservoir 62; a third port 128 connected by line 130 through to valve 132; and a fourth port 134 connected by line 136 to valve 138. Connected in series with each valve 132, 138 is a bubble chamber component 46, a check valve 140, a needle valve 142 and a purge valve 144. The flow control system associated with valve 132 is connected to a terminal 146 that is adapted to be connected to a first (low) calibrating gas reservoir and the flow control system associated with valve 138 is connected to a second (high) calibrating gas terminal 148.

Flow control 52 has three operative positions. In a first position port 80 is connected to port 82 and ports 120, 124, 128 and 134 are blocked. In a second position, port 120 is connected to port 82, port 128 is connected to port 80, and ports 124 and 134 are blocked. In the third position, port 124 is connected to port 82, port 134 is connected to port 80, and ports 120 and 128 are blocked.

The $PCO_2$ electrode 26 includes a section of pH sensitive glass over which is disposed a membrane that is permeable to carbon dioxide gas and that electrode supplies an output over line 150 to electrical circuitry 152 which has balance control 154 and slope control 156 and which produces an output for display by digital display 158. The $PO_2$ electrode 24 produces a current at a constant polarizing voltage which is directly proportionnal to the tension of oxygen diffusing to its reactive cathode surface and that electrical signal is applied over line 160 to electrical circuitry 162 which includes balance control 164 and slope control 166 and which produces an output for display for digital display 168. The pH electrode 22 includes a capillary section 88 of pH sensitive glass through which the sample is drawn. The reference electrode 28 is disposed in a saturated KCl solution and electrical contact is established between reference electrode 28 and the sample in capillary 88 of measuring electrode 22 through leak junction membrane 90. Electrical signals from pH electrode 22 and the reference electrode applied over lines 170, 172 to electrical circuitry 174 which similarly has balance control 176 and slope control 178 and its resulting output is displayed by digital display 180.

Figure 5:
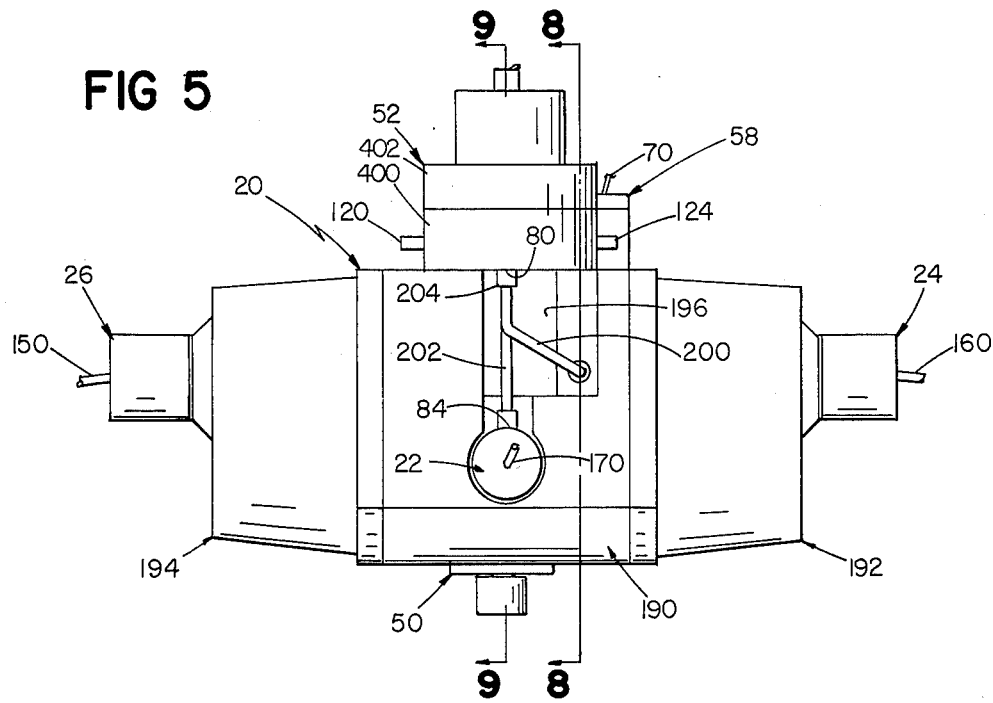
FIG. 5 is a top view of the tank and valve assembly employed in the system shown in FIG. 1.
Figure 6:
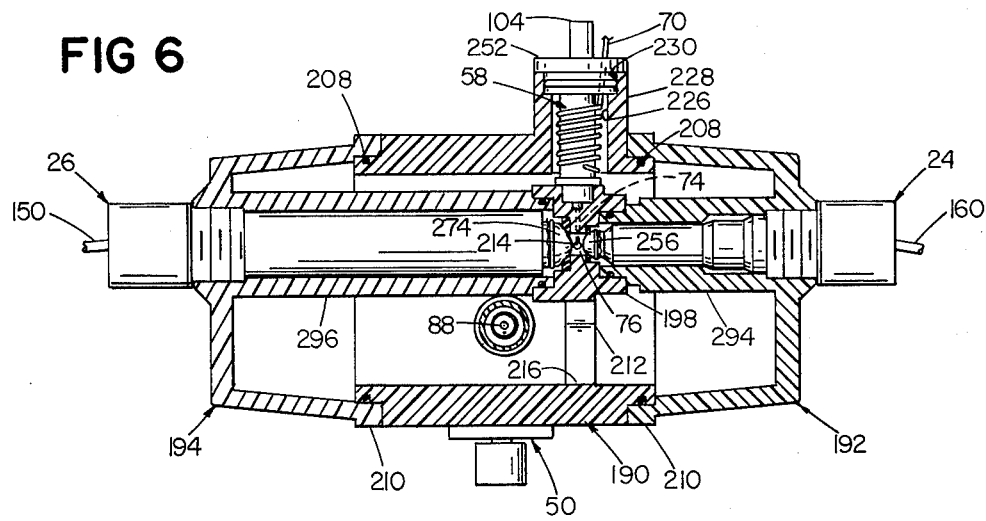
FIG. 6 is a sectional view taken along the line 6—6 of FIG. 3.

Further details of portions of the sample flow path and the interrelated electrode structure arrangement may be seen with reference to FIGS. 5-9. The tank assembly 20 is made of acrylic plastic and as indicated in FIGS. 5 and 6, includes a center member 190 and end members 192 and 194. As indicated in FIG. 5, center member 190 has a recess 196 in its upper surface. Conduit tubes 200 and 202 are disposed in the recess and one end of each is detachably connected to fittings 204 and 206 that define ports 80 and 82, respectively, of control valve 52. As shown in FIG. 6, center member 190 has an annular flange at each end, in each of which is disposed a sealing O-ring 208. Each end member 192, 194 has an annular end surface 210 which mates in sealing relation with O-ring 208 and is secured in place by bolts (not shown). Center member 190 includes a transversely extending web 212. Formed in web 212 is measuring chamber 76 in the form of a cylinder 0.2 inch in diameter. Entrance passage 74, of about 0.03 inch diameter, extends horizontally in tangential relation into chamber 76. Exit passage 78, of about 0.1 inch diameter, extends vertically upwardly from chamber 76 to conduit 200. A monitoring electrode 214 extends vertically downwardly from measuring chamber 76 to a point external of center member 190. Also formed in web 212 is a relatively large aperture 216 (FIG. 8), a small circular aperture which supports a mercury thermometer 218; and an arcuate aperture 220.

The entrance end of inlet passage 74 is enlarged and receives a seal member 222 which in turn receives the tip 224 of sample heater assembly 58. That heater assembly is disposed in bore 226 that is axially aligned with passage 74 and extends outwardly in boss 228. The heater assembly 58 is secured on boss 228 so that the tip 224 of the heater assembly is seated in sealing engagement with seal member 222.

Figure 7:
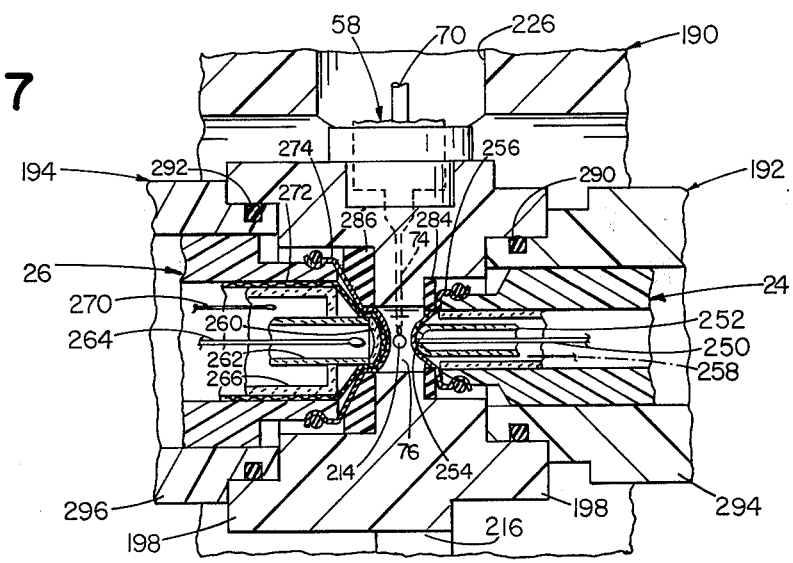
FIG. 7 is an enlarged sectional view showing details of a measuring cell and associated sensor electrodes.

Further details of the sample chamber may be seen with reference to FIG. 7. Oxygen electrode assembly 24 includes a cathode wire 250 sealed in glass envelope 252 so that only its tip 254 is exposed at the end of envelope 252. This reactive surface 254 is covered by membrane 256 which is permeable to oxygen but not to contaminants and reduceable ions of the sample. a silver/silver chloride anode 258 is incorporated in the electrode assembly and the assembly is connected by cable 160 to the electronics section 12. The carbon dioxide sensor includes a pH sensitive glass membrane 260 at its tip which forms the end wall of an inner chamber 262 in which is housed silver/silver chloride electrode 264. Outer chamber 266 is filled with electrolyte and contains a silver/silver chloride reference electrode 270. Disposed over the end of the electrode assembly is a spacer membrane 272 and a membrane 274 that is permeable to carbon dioxide gas but not to ions. Cable 150 connects the electrode to the electronic circuitry 12. The two electrodes are seated on sealing members 284, 286 received in recesses of the chamber structure and sealed in place. Similar seals 290, 292 carried by the inwardly extending electrode housing portions 294, 296 of the end members 192, 194 of the tank assembly 20 sealingly engage annular flanges of the center member 190.

The pH electrode 22 is disposed in tube 298 and, as indicated in FIG. 9, includes a capillary section 300 in which is disposed section 88 of pH sensitive glass. A silver/silver chloride half cell 302 is disposed in electrolyte chamber 304 that surrounds capillary tube 300. The capillary tube has an inlet port 306 at its upper end and a tip portion 308 at its lower end that is received in seal 310 carried by member 312 that provides a leak junction flow path. The flow path in member 312 is about 0.04 inch diameter and has a jog defined by arms 314, 316 which are disposed at an angle of 60° to one another and extend to port 318. Cooperating member 320 carries membrane 90 which is a disc of polycarbonate material about 10 microns in thickness that has a multiplicity of parallel passages, each about 0.1 micron in diameter. Member 320 is carried by frame 322 and is arranged to be secured in place by clamp screw 324 so that membrane 90 is compressed over port 318 with straight line force without subjecting the membrane 90 to twisting or shear force to provide seal of both the sample channel 328 and the electrolyte channel 326 that is formed in member 320. Connected to electrolyte channel 326 by conduit 92 is electrolyte reservoir 94 in which is disposed reference electrode 28. That electrode contains a saturated calomel half cell and is connected to measuring circuitry by cable 172.

Additional details of the sample heater structure 58 may be seen with reference to FIGS. 10 and 11. That heater structure includes a body 350 that has a flange 352 and carries a first O-ring seal 354 adjacent its outer end and a second O-ring seal 356 adjacent its inner end. Formed between seals 354 and 356 is an itermediate or arbor portion which has a spiral groove 358 in its outer surface that is interrupted by a plurality of axially extending slots 360. Body 350 has a recess 362 in which the end 364 of tubing 366 is received. Tubing 366 is 0.034 inch I.D. polyvinyl chloride and is brought out through one of slots 360 and then wound forwardly on groove 358 to form a first spiral layer.

A sleeve 368 which is disposed over the first spiral layer has spiral groove 370 that is similarly interrupted by axially extending slots 372; and the tubing 366 is wound rearwardly on spiral groove 370 towards flange 352, then carried through exit passage 374 and sealed in place in flange 352. In assembly, the heater assembly is inserted into bore 226 with O-ring 354 in sealing engagement with counterbore 230 and O-ring 356 in sealing engagement with insert 376. Tip 224 is seated in sealing engagement with seal 222 in alignment with passage 74. The flow of tempering water is into passage 380, then out through axial slots 360 around the inner spiral of the tubing and then through slots 372 and around the outer spiral. The water then flows from bore 226 past insert 376 and through arcuate aperture 220 into the jacket chambers on either side of measuring chamber 76 and out through connections 106, 108 for return to the circulator 40. This flow of tempering fluid bathes pH electrode housing 298 and maintains that measuring cell at the same stable temperature at which cell 76 is maintained. The sample fluid flows from tip 36 through conduit 70 into and through the two spiral layers of the heater assembly and then into passage 74 for flow into measuring chamber 76. From measuring chamber 76 flows upwardly through vertical passage 78 to conduit 200 and port 80 of valve 52.

Details of the valve 52 may be seen with reference to FIGS. 12-19. That valve includes a Delrin base 400 and a cap 402 secured together by bolts 404. Secured in base 400 are fittings 204, 206 that define ports 80 and 82, and similar fittings that define ports 120, 124, 128 and 134. Fitting 204 communicates with port 406 in valve base 400, fitting 206 communicates with port 408; port 120 communicates with port 410, port 124 communicates with port 412; port 128 communicates with port 414; and port 134 communicates with port 416. Arcuate groove 418 extends from port 406 past port 416 to a termination in the 1½ centimeter diameter port circle 420 at point 422. Seated on surface 424 is a seal disc 426 of 50 Shore A durometer neoprene rubber, disc 426 having a diameter of 4 centimeters and a thickness of about 1½ millimeters. Formed in disc 426 as indicated in FIG. 15 are a set of seven passages 430–436 that are aligned with base ports 406–422, respectively.

Seal disc 426 is clamped on surface 424 by valve cap 402. Housed within cap 402 is selector structure 440 that includes an outwardly extending shaft portion 442, bearing portion 444, collar 446, seat surface 448 and selector disc portion 450 that has two grooves 452, 454 formed in its face as indicated in FIG. 13. Groove 452 extends from the central point 456 to a point 458 in port circle 460; while groove 454 extends from point 462 on the port circle 460 to point 464 also on the port circle 460. The surface of disc portion 450 has a Teflon coating 466.

Housed within cap 402, as indicated in FIG. 10, is a nylon washer 470 on which is seated spring 472 which biases the face of selector disc 450 against seal disc 426. Fittings 100 and 102 are connected to cap 402 and permit the flow of tempering water therethrough.

Diagrams of three operative positions of the valve are shown in FIGS. 17–19. In the analysis position shown in FIG. 17, selector disc 450 is positioned so that radial groove 452 is in communication through seal disc port 436 with arcuate channel 418, completing a flow passage from port 80 through arcuate channel 418 and then radially inward through groove 452 to port 82. Valve ports 120, 124, 128 and 134 are all sealed by selector disc 450 overlying corresponding ports in seal disc 426.

In a first calibrating position shown in FIG. 18 (selector disc 450 being rotated 45°), radial groove 452 connects port 82 via seal disc port 432 to fitting 120; while tangential groove 454 connects fitting 128 to port 80; ports 124 and 134 remaining sealed by the interengagement of selector disc 450 and seal disc 426. In the third position of the valve (FIG. 19) a second calibrating position, selector disc 450 is rotated through a further 45° angle. In this position port 82 is placed in communication with port 124 through radial groove 452; and port 80 is in communication with port 134 through tangential groove 454; and ports 120 and 128 are sealed.

When it is desired to perform a blood gas analysis, valve 52 is placed in the position shown in FIG. 17 and a blood sample is introduced into measuring chambers 76 and 88 by placing sample entrance 36 in its first position, immersing its tip in a sample container and operating peristaltic pump 42. The pump draws the sample through conduit 70, through the two spirals of heater 56, conduit 74, chamber 76, conduits 78 and 200, valve passages 418 and 452, conduits 202 and 84, capillary passage 300 through leak junction passage 328 to conduit 96. This flow path configuration requires a sample volume of less than five hundred microliters for simultaneous pH, $PO_2$ and $PCO_2$ measurements on the same sample. The sample tip 36 is placed in flush fluid in chambers 38 and translating circuitries 152, 162 and 174 are released to respond to signals from electrodes 22, 24, 26 and 28 and to translate the resulting electrical signals to output values which are applied to digital displays 158, 168 and 180. The oxygen electrode 24 produces a current which is directly proportional to the tension of oxygen diffusing through membrane 256 carried by the electrode assembly. The carbon dioxide electrode assembly 26 senses a change in carbon dioxide concentration as a function of pH, the carbon dioxide diffusing across membrane 274 and develops a voltage exponentially related to $PCO_2$ which is translated by circuitry 152 to produce an output signal which is applied to digital display 158. The pH system includes electrodes 22 and 28 and a potential difference between the surfaces of glass membrane 88 is applied via electrode 22, 28 to translating circuitry 174 which generates an output for application to digital display 180. As soon as the data is obtained, pump 42 is operated to draw flush fluid through the entire sample path in a cleaning operation in preparation for the next sample analysis. If desired, pump 42 may be driven manually by disc 44 enabling precise adjustment of a sample in the transparent measuring cell or serial movement of the sample into cell 76 and then into cell 88 for separate microsample (175 mmicroliter) analyses.

In preparation for such analyses, the oxygen and carbon dioxide sensors 24, 26 are calibrated with two gases from sources connected to fittings 146, 148; and the pH sensor 22 is calibrated with buffer liquids from sources 60 and 62. With the valve 52 in the analysis position (FIG. 17) and with sample tip 36 in flush solution in reservoir 38, peristaltic pump 42 is operated to draw flush solution through the system in a cleaning operation. Valve 52 is then moved to a first calibration position (FIG. 18) in which measuring chamber 76 is connected to the low gas source and pH measuring chamber 88 is connected to buffer source 60 (pH 7.384). In this valve position, the gas flowing through measuring chamber 76 has a mixture of about five percent carbon dioxide, twelve percent oxygen and the balance nitrogen, and the carbon dioxide electrode translating circuitry 152 is adjusted by balance control 154 in a zeroing operation. The pH circuitry 174 is also adjusted by its balance control 176 in a zeroing operation. After the pH and carbon dioxide electrode systems are zeroed, the valve is moved to the third position (FIG. 19) in which position a high gas source connected to fitting 148 (about 10 percent carbon dioxide, no oxygen and the remainder nitrogen) is applied to measuring chamber 76, and chamber 88 is connected to the low buffer (pH 6.84) source 62. Peristaltic pump 42 is operated to place the low buffer in chamber 88. With calibrating gas from the second source flowing through chamber 76, the balance control 164 of the oxygen translating circuitry 162 is adjusted and at the same time the slope control 156 of carbon dioxide translating circuitry 152 is adjusted. The pH electrode circuitry 174 is sloped through adjustment of slope control 178. After the oxygen system has been zeroed and the carbon dioxide and pH electrode systems have been adjusted for slope, valve 52 is returned to its first calibrating position (FIG. 18) and a slope adjustment for the oxygen system is made utilizing the calibrating gas from the first source and control 156.

When the response of the electrode systems have been satisfactorily calibrated, valve 52 is returned to the analysis position (FIG. 17) and the instrument is ready for an analysis sequence. As discussed above, sample tip 36 is removed from the flush fluid and immersed in a blood sample to be analyzed, pump 42 is operated to induct about 500 microliters of blood through the preheater 56 into the measuring chambers 76 and 88 and past reference electrode junction 50. After the sample has been so flowed into those chambers, the translating circuits are released and measurements of pH, $PCO_2$ and $PO_2$ are simultaneously obtained on the same microsample. After the sample has been inducted, the sample tip 36 is replaced in the flush solution in chamber 38 and after the analysis values are displayed, the sample is flushed from the measuring chambers 76 and 88 by operation of pump 42, flush solution being concurrently drawn through the system in a cleaning operation. Calibration of the electrode systems may be periodically checked by placing the value 52 in a calibrate position and allowing the selected calibrating gas to flow through chamber 76 while the correspondingly selected buffer liquid is pumped through chamber 88, the displays being released so that the operator may check instrument balance.

While a particular embodiment of the invention has been shown and described, it is not intended that the invention be limited to the disclosed embodiment or to details thereof and departures may be made therefrom within the spirit and scope of the invention as defined in the claims.

What is claimed is:

1. An analysis system for measuring a plurality of parameters of a fluid sample comprising a tempering chamber for containing a tempering fluid to maintain a stable temperature environment in the chamber, first and second measuring systems, each said measuring system including an electrode assembly that has an elongated electrode housing and a sensing electrode disposed in said housing, first and second flow through measuring cells corresponding respectively to said first and second measuring systems and mounted in said tempering chamber, each said measuring cell having an inlet port, an outlet port and a flow through passage between said inlet and outlet ports, the sensing electrode of each measuring system being disposed immediately adjacent its corresponding measuring cell, said measuring cells being located centrally within said tempering chamber and said elongated electrode housings extending into said tempering chamber with the axes of said elongated electrode housings disposed generally perpendicular to one another, system inlet structure including an entrance port, conduit connecting said entrance port of said system inlet structure to the inlet ports of both of said measuring cells, positive displacement pump structure, conduit connecting the outlet ports of both of said measuring cells to said positive displacement pump structure, and flush fluid supply, said system inlet structure being movable between a first position where its said entrance port is exposed to receive a fluid sample to be analyzed and a second position where its said entrance port is immersed in flush fluid in said flush fluid supply, operation of said pump with said system inlet structure in said first position adapted to flow a sample through both of said measuring cells and operation of said pump with said system inlet structure in said second position flowing flush fluid through both of said measuring cells.

2. The system as claimed in claim 1 and further including exposed detachable conduit connecting the outlet port of one of said measuring cells and the inlet port of the other of said measuring cells, said detachable conduit being external of said tempering chamber and facilitating alternate access to said measuring cells as desired.

3. The system as claimed in claim 1 and further including a control device mounted on said tempering chamber connected between said first and second measuring cells, said control device having a first mode in which both said measuring cells are in fluid communication with said system inlet structure and a second mode in which said measuring cells are isolated from one another and in communication with corresponding auxiliary fluid inlet ports.

4. The system as claimed in claim 1 and further including heater structure mounted on said tempering chamber and connected in series between said system inlet structure and the inlet ports of said measuring cells.

5. The system as claimed in claim 4 wherein said heater structure includes structure supporting two superimposed sample conduit spiral windings and a chamber in communication with said tempering chamber for receiving tempering fluid for flow across and in intimate contact with the superimposed sample conduit windings.

6. The system as claimed in claim 1 wherein said first measuring system is coupled to said first measuring cell for measuring a gaseous parameter of the fluid sample and said second measuring system is coupled to the second measuring cell for measuring the pH of the fluid sample, said second measuring system further including a reference electrode interface mounted on said tempering chamber and in communication with the flow path between said second measuring cell and said positive displacement pump.

7. The system as claimed in claim 6 wherein said reference electrode interface includes structure mounted on said tempering chamber defining a portion of the flow path between the second measuring cell and said positive displacement pump, said flow path defining structure having an opening therein, a detachable support structure defining an electrolyte connection to a reference electrode, and a flow control member carried by said support structure and disposed over the opening of said flow path defining structure for providing a controlled liquid flow path for establishing an ionic junction between the electrolyte and sample material in said flow path.

8. The system as claimed in claim 7 and further including clamp structure arranged to impose clamping force along the axis defined by the openings between which said flow control member is disposed.

9. The system as claimed in claim 8 wherein said flow control member has a multiplicity of substantially parallel passages of equal length that extend through said member, so that a multiplicity of ionic junctions are provided between the electrolyte and the sample material to be analyzed.

10. The system as claimed in claim 9 wherein said second structure is a replaceable component and said flow control member is secured on said second member.

11. The system as claimed in claim 3 and further including conduits external of said tempering chamber detachably connecting each said measuring cell to said control device.

12. An analysis system for measuring a plurality of parameters of a fluid sample comprising a tempering chamber for containing a tempering fluid to maintain a stable temperature environment in the chamber, first and second measuring systems, each said measuring system including an electrode assembly that has an electrode housing and a sensing electrode disposed in said housing, first and second flow through measuring cells corresponding respectively to said first and second measuring systems and mounted in said tempering chamber, each said measuring cell having an inlet port, an outlet port and a flow through passage between said inlet and outlet ports, the sensing electrode of each measuring system being disposed immediately adjacent its corresponding measuring cell, said measuring cells being located centrally within said tempering chamber, system inlet structure including an entrance port, conduit connecting said entrance port of said system inlet structure to the inlet ports of both of said measuring cells, a control device mounted directly on said tempering chamber and connected between said first and second measuring cells, said control device having a first mode in which both said measuring cells are in fluid communication with said system inlet structure and a second mode in which said measuring cells are isolated from one another and in communication with corresponding auxiliary fluid inlet ports, heater structure mounted directly on said tempering chamber and connected in series between said system inlet structure and the inlet ports of said measuring cells, said control device and said heater structure each having a chamber in communication with said tempering chamber for receiving tempering fluid for flow therethrough, positive displacement pump structure, conduit connecting the outlet ports of both of said measuring cells to said positive displacement pump structure, and flush fluid supply, said system inlet structure being movable between a first position where its said entrance port is exposed to receive a fluid sample to be analyzed and a second position where its said entrance port is immersed in flush fluid in said flush fluid supply, operation of said pump with said system inlet structure in said first position adapted to flow a sample through both of said measuring cells and operation of said pump with said system inlet structure in said second position flowing flush fluid through both of said measuring cells.

13. The system as claimed in claim 12 wherein said first measuring system is coupled to said first measuring cell for measuring a gaseous parameter of the fluid sample and said second measuring system is coupled to the second measuring cell for measuring the pH of the fluid sample, said second measuring system further including a reference electrode interface mounted on said tempering chamber and in communication with the flow path between said second measuring cell and said positive displacement pump.

14. The system as claimed in claim 13 wherein the volume of said flow path between said heater structure and said reference electrode interface is less than 500 microliters.

15. The system as claimed in claim 3 and further including a third measuring system that includes an electrode assembly that has an elongated electrode housing and a sensing electrode disposed in said housing, the elongated electrode housing of said third measuring system extending into said tempering chamber with its axis disposed in alignment with the axis of the elongated electrode housing of said first measuring system and the sensing electrode of said third measuring system being disposed immediately adjacent said first measuring cell, said first and third measuring systems being coupled to said first measuring cell for measuring two different gaseous parameters of the fluid sample and said second measuring system being coupled to said second measuring cell for measuring the pH of the fluid sample.

* * * * *